(12) United States Patent
Patrick et al.

(10) Patent No.: US 7,524,274 B2
(45) Date of Patent: Apr. 28, 2009

(54) TISSUE POSITIONING SYSTEMS AND METHODS FOR USE WITH RADIATION THERAPY

(75) Inventors: Timothy J. Patrick, Alpharetta, GA (US); James B. Stubbs, Alpharetta, GA (US)

(73) Assignee: Cytyc Corporation, Marlborough, MA (US)

( * ) Notice: Subject to any disclaimer, the term of this patent is extended or adjusted under 35 U.S.C. 154(b) by 1031 days.

(21) Appl. No.: 10/704,161

(22) Filed: Nov. 7, 2003

(65) Prior Publication Data

US 2005/0101860 A1 May 12, 2005

(51) Int. Cl.
*A61N 5/00* (2006.01)

(52) U.S. Cl. ............................................. 600/1
(58) Field of Classification Search .................. 600/1–8
See application file for complete search history.

(56) References Cited

U.S. PATENT DOCUMENTS

| | | | | |
|---|---|---|---|---|
| 3,324,847 | A | 6/1967 | Zoumboulis | 128/1.2 |
| 3,872,856 | A | 3/1975 | Clayton | 128/1.2 |
| 4,417,576 | A | 11/1983 | Baran | 128/207.15 |
| 4,706,652 | A | 11/1987 | Horowitz | 128/1.2 |
| 4,754,745 | A | 7/1988 | Horowitz | 128/1.2 |
| 4,763,642 | A | 8/1988 | Horowitz | 128/1.2 |
| 4,821,725 | A | 4/1989 | Azam et al. | 128/420 A |
| 4,867,741 | A | 9/1989 | Portnoy | 604/10 |
| 5,030,195 | A | 7/1991 | Nardi | 600/7 |
| 5,084,001 | A | 1/1992 | Van't Hooft et al. | 600/3 |
| 5,084,015 | A | 1/1992 | Moriuchi | 604/96 |
| 5,106,360 | A | 4/1992 | Ishiwara et al. | 600/2 |
| 5,112,303 | A | 5/1992 | Pudenz et al. | 604/49 |
| 5,152,747 | A | 10/1992 | Olivier | 604/93 |
| 5,236,410 | A | 8/1993 | Granov et al. | 600/12 |
| 5,429,582 | A | 7/1995 | Williams | 600/2 |
| 5,484,384 | A | 1/1996 | Fearnot | 600/3 |
| 5,503,613 | A | 4/1996 | Weinberger | 600/3 |

(Continued)

FOREIGN PATENT DOCUMENTS

EP 0340881 11/1989

(Continued)

OTHER PUBLICATIONS

Ashpole, R.D. et al., "A New Technique of Brachytherapy for Malignant Gliomas with Caesium-137: A New Method Utilizing a Remote Afterloading System," Clinical Oncology, vol. 2, 333-7 (1990).

(Continued)

*Primary Examiner*—John P Lacyk
(74) *Attorney, Agent, or Firm*—Heather Larson (57) ABSTRACT

A system for treating tissue surrounding a resected cavity that is subject to a proliferative tissue disorder is provided. The system includes a tissue fixation device including a catheter body member having a proximal end, a distal end, an inner lumen, and an expandable surface element disposed proximate to the distal end of the body member, the expandable surface element sized and configured to reproducibly position tissue surrounding a resected tissue cavity in a predetermined geometry upon expansion. After expansion of the expandable surface element within a resected tissue cavity, an external radiation device positioned outside the resected cavity delivers a dose of radiation to the tissue surrounding the expandable surface element.

42 Claims, 5 Drawing Sheets

U.S. PATENT DOCUMENTS

| | | | |
|---|---|---|---|
| 5,566,221 A | 10/1996 | Smith et al. | 378/145 |
| 5,611,767 A | 3/1997 | Williams | 600/2 |
| 5,662,580 A | 9/1997 | Bradshaw et al. | 600/3 |
| 5,707,332 A | 1/1998 | Weinberger | 600/3 |
| 5,713,828 A | 2/1998 | Coniglione | 600/7 |
| 5,720,717 A | 2/1998 | D'Andrea | 604/21 |
| 5,764,723 A | 6/1998 | Weinberger et al. | 378/65 |
| 5,782,742 A | 7/1998 | Crocker et al. | 600/3 |
| 5,785,688 A | 7/1998 | Joshi et al. | 604/141 |
| 5,993,374 A | 11/1999 | Kick | 600/8 |
| 6,036,631 A | 3/2000 | McGrath et al. | 600/3 |
| 6,048,299 A | 4/2000 | Hoffmann | 600/3 |
| 6,120,523 A | 9/2000 | Crocker et al. | 606/192 |
| 6,149,574 A | 11/2000 | Trauthen et al. | 600/3 |
| 6,176,821 B1 | 1/2001 | Crocker et al. | 600/3 |
| 6,200,257 B1 | 3/2001 | Winkler | |
| 6,261,320 B1 | 7/2001 | Tam et al. | 623/1.15 |
| 6,287,249 B1 | 9/2001 | Tam et al. | 600/3 |
| 6,413,204 B1 | 7/2002 | Winkler et al. | |
| 6,419,692 B1 | 7/2002 | Yang et al. | 623/1.15 |
| 6,458,069 B1 | 10/2002 | Tam et al. | 600/3 |
| 6,471,630 B1 | 10/2002 | Sioshansi et al. | 600/1 |
| 6,487,438 B1 | 11/2002 | Widmark et al. | 600/431 |
| 2003/0028097 A1 | 2/2003 | D'Amico et al. | 600/427 |
| 2003/0114878 A1 | 6/2003 | Diederich et al. | 606/192 |

FOREIGN PATENT DOCUMENTS

| | | |
|---|---|---|
| EP | 0867200 | 9/1998 |
| GB | 2105201 | 3/1983 |
| WO | 9210932 | 7/1992 |
| WO | 9309724 | 5/1993 |
| WO | 9719723 | 6/1997 |
| WO | 9812979 | 4/1998 |
| WO | 9911325 | 3/1999 |
| WO | 9933515 | 7/1999 |
| WO | 9942163 | 8/1999 |
| WO | WO 00/22904 | 4/2000 |

OTHER PUBLICATIONS

A. Bex et al., "A Systen For Focal Intracavitary Irradiation Of Bladder Cancer With Remote Iridium-192 Afterloading", 21 Eur Urol 1992, 245-249 (1992).

Chun, M. et al. "Interstitial Iridium-192 Implantation for Malignant Brain Tumours. Part II: Clinical Experience," *The British Journal of Radiology*, vol. 62, 158-62 (1989).

Garfield, J. et al., "Postoperative Intracavitary Chemotherapy of Malignant Gliomas," *J. Neurosurg.*, vol. 39, 315-22 (Sep. 1973).

Gutin, P. et al., "Brachytherapy of Recurrent Malignant Brain Tumors With Removable High-Activity Iodine-125 Sources," *J. Neurosurg.*, vol. 60, 61-8 (1984).

Johannesen, T.B. et al., "Intracavity Fractionated Balloon Brachytherapy in Glioblastoma," *Acta Neurochir (Wien)*, vol. 141, 127-33 (1999).

Leibel, S. et al., "The Integration of Interstitial Implantation Into the Preliminary Management of Patients With Malignant Gliomas: Results of a Phase II Northern California Oncology Group Trial," *Am. J. Clin. Oncol. (CCT)*, vol. 10, No. 2, p. 106 (1987).

Roberts, D. et al., "Interstitial Hyperthermia and Iridium Brachytherapy in Treatment of Malignant Glioma," *J. Neurosurg.*, vol. 64, 581-7 (1986).

Wu, A. et al., "Interstitial Iridium-192 Implantation for Malignant Brain Tumours. Part 1: Techniques of Dosimetry Planning," *The British Journal of Radiology*, vol. 62, 154-7 (1989).

TISSUE POSITIONING SYSTEMS AND METHODS FOR USE WITH RADIATION THERAPY

BACKGROUND OF THE INVENTION

The invention relates generally to systems and methods for use in treating proliferative tissue disorders, and more particularly to systems and methods for the treatment of such disorders in the breast by positioning tissue and applying radiation.

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including permanent or temporary interstitial brachytherapy, and external-beam radiation.

Brachytherapy refers to radiation therapy delivered by a spatially confined radioactive material inserted into the body at or near a tumor or other proliferative tissue disease site. For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. In brachytherapy, radiation doses are highest in close proximity to the radiotherapeutic source, providing a high tumor dose while sparing surrounding normal tissue. Interstitial brachytherapy is useful for treating malignant brain and breast tumors, among others.

Williams U.S. Pat. No. 5,429,582, entitled "Tumor Treatment," describes a Brachytherapy method and apparatus for treating tissue surrounding a surgically excised tumor with radioactive emissions to kill any cancer cells that may be present in the tissue surrounding the excised tumor. In order to implement the radioactive emissions, Williams provides a catheter having an inflatable balloon at its distal end that defines a distensible reservoir. Following surgical removal of a tumor, the surgeon introduces the balloon catheter into the surgically created pocket left following removal of the tumor. The balloon is then inflated by injecting a fluid having one or more radionuclides into the distensible reservoir via a lumen in the catheter.

While brachytherapy procedures have successfully treated cancerous tissue, alternative radiation treatments are sometimes preferable, including radiation therapies which are delivered from a source external to the patient. For example, External Beam Radiation Therapy involves directing a "beam" of radiation from outside the patient's body, focused on the target tissue within a patient's body. The procedure is painless and often compared to the experience of having an x-ray.

As with any radiation therapy, the goal is to deliver a prescribed dose of radiation to the target tissue while minimizing damage to healthy tissue. More recent advances in radiation therapy such as Three-Dimensional Conformal Radiation Therapy (3DCRT) and Intensity Modulated Radiation Therapy (IMRT) have increased the precision of external radiation therapy with sophisticated shaping and directing of therapeutic radiation beams. In addition, imaging techniques allow delineation of a more complex planning target volume ("PTV", PTV refers to the mass of tissue which includes both the residual malignancy as well as a margin of surrounding healthy tissue). These imaging procedures use cross-sectional imaging modalities including computed tomography (CT), magnetic resonance imaging (MRI), positron emission tomography (PET), single photon emission computed tomography (SPECT) and portal imaging to visualize target tissue. Treatment planning software combines the anatomical details from the imaging procedures and a PTV outlined by the physician, to optimize the number, size and shape of the radiotherapy beams used to treat the patient. The goal of the treatment plan is to deliver a conformal radiation dose to the PTV and minimize the radiation delivered to adjacent normal tissue outside the PTV.

In use, 3DCRT provides radiation beams shaped to "conform" to a target tissue volume, and with the ability to visualize and to arrange the radiation therapy beams, physicians can maximize coverage of the target tissue and minimize exposure to normal tissue. IMRT similarly conforms radiation beams to the size, shape and location of the target tissue by using hundreds to thousands of small, modulated radiation beams, striking the target tissue with varying intensities. The multitude of beams treats the target tissue and minimizes damage to healthy tissue. Yet, even the most advanced procedures require the patient and the target tissue to be properly positioned, and in some cases immobilized. Unfortunately, the irregular surface of a cavity created by the resection of tissue can make it difficult for the imaging techniques to determine the exact location of the target tissue, and even with the opportunity to completely map the target area, the unsupported tissue surrounding the resected cavity may shift during the procedure or between imaging and treatment, particularly where the treatment regimen involves radiation doses provided over the course of several days or weeks.

As a result, there is still a need for additional methods for delivering radiation from an external radiation source to tissue adjacent to a resected tissue cavity with a desired accuracy and without over-exposure of surrounding tissue.

SUMMARY OF THE INVENTION

The present invention provides methods, systems and devices for treating a proliferative tissue disorder by positioning tissue surrounding a resected tissue cavity and applying external radiation. The method includes first surgically resecting at least a portion of proliferative tissue and thereby creating a resection cavity. A tissue fixation device having an expandable surface is then provided, the expandable surface being sized and configured to reproducibly position tissue surrounding the resection cavity in a predetermined geometry upon expansion of the expandable surface into an expanded position. Next, the expandable surface is positioned within the resection cavity and the expandable surface is expanded to position the tissue surrounding the resection cavity in the predetermined geometry. Finally, an external radiation treatment is applied to the tissue surrounding the resection cavity.

In another aspect of the invention, the resected cavity and the expanded tissue fixation device positioned therein can be visualized in three dimensions. The invention can also preferably include applying at least one of an external beam radiation treatment, a three-dimensional conformational radiation therapy treatment, and an intensity modulation radiation therapy treatment. The method may further include repeating the treatment steps several times during a treatment regimen.

In one embodiment, the expandable surface of the tissue fixation device includes a solid distensible surface defining a closed distensible chamber, and in a further embodiment the tissue fixation device is a balloon catheter. In yet a further embodiment, a second balloon can be positioned with in the first balloon. The balloons can be expanded with a variety of mediums including a non-radioactive substance. In other aspects of the invention, a treatment material is used to expand the balloon. The treatment material can include a drug such as a chemotherapy drug which is delivered through the wall of the balloon to the surrounding tissue. In an alternative embodiment the expandable surface is created by an expandable cage.

In another aspect of the present invention, fiducial markers can be positioned on the tissue fixation device to determine the spatial location of the device and the surrounding PTV. For example, by determining the spatial position of the markers relative to the origin of a coordinate system of the treatment room (e.g., relative to the treatment beam isocenter or beam source), the location of the device and the PTV can be compared to their desired locations. If there are any changes in the PTV or in the location of the device, adjustments can be made to the position of the patient's body, the device, and/or the direction and/or shape of the planned radiation beams prior to initiation of the radiation fraction. The fiducial markers and their detection systems can be radio-opaque markers that are imaged radiographically or transponders that signal their position to a receiver system.

Another embodiment of the present invention includes a system for treating tissue surrounding a resected cavity that is subject to a proliferative tissue disorder. The system includes a tissue fixation device having a catheter body member with a proximal end, a distal end, an inner lumen, and an expandable surface element disposed proximate to the distal end of the body member, the expandable surface element being sized and configured to reproducibly position tissue surrounding a resected tissue cavity in a predetermined geometry upon expansion. An external radiation device is positioned outside the resected cavity such that the external radiation device can deliver a dose of radiation to the tissue surrounding the expandable surface element. With the tissue fixation device positioned within the resected tissue cavity and expanded to position the surrounding tissue, the accuracy of radiation from the external radiation device is greatly improved.

In yet a further embodiment, the invention includes a device for treating a proliferative tissue disorder after a lumpectomy procedure. The device including an elongate body member having an open proximal end defining a proximal port, a distal end and an inner lumen extending from the open proximal end, the elongate body member being sized for delivering an expandable surface element into a resection cavity created by a lumpectomy procedure. A spatial volume is defined by an expandable surface element disposed proximate to the distal end of the body member, the expandable surface element sized and configured to reproducibly position tissue surrounding a resected tissue cavity in a predetermined geometry upon expansion. The expandable surface element is size to fill a tissue cavity created in a breast during a lumpectomy procedure so as to position the surrounding tissue and allow an external radiation source to accurately deliver a dose of radiation.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides systems and methods for treating proliferative tissue disorders, such as malignant tumors of the breast, by surgically resecting at least a portion of the proliferative tissue to create a resection cavity, followed by external radiation therapy of residual tumor margin. To improve the accuracy of the radiation treatment, a tissue fixation device is provided to position and/or stabilize the tissue surrounding the resected cavity.

External radiation therapies rely on precise imaging and/or targeting techniques, and any movement of the target tissue can introduce error. Patient positioning is often critical and great measures are taken to position and immobilize patients, including for example, marking the patient's skin and using foam body casts. Yet even with the patient immobilized, shifting of the target tissue still presents a problem, including for example, shifting of tissue as a result of the patient breathing and inconsistencies in the positioning of the patient's body between radiotherapy fractions.

Tissue cavities present an even greater difficulty because the tissue surrounding the cavity is often soft, irregular tissue which lacks the support usually provided by adjacent tissue. The irregular surface of the cavity wall, including the residual tumor margin, is therefore difficult to image. Unpredictable shifting of the tissue surrounding the cavity, possibly caused by slight patient movement, can further complicate the procedure and result in unacceptable movement of the target tissue. For example, where the target tissue changes position after visualization, but before radiation treatment, the shifting tissue may result in radiation beams encountering primarily healthy tissue. As a result, the residual tumor margin may be substantially untreated, while healthy tissue may be damaged by the treatment. The present invention overcomes these prior art problems by providing a tissue positioning device which can be inserted into the resected cavity and expanded to position the surrounding tissue in a predetermined geometry. The methods of the present invention also facilitate tissue imaging by positioning tissue against a defined surface.

Figure 1:
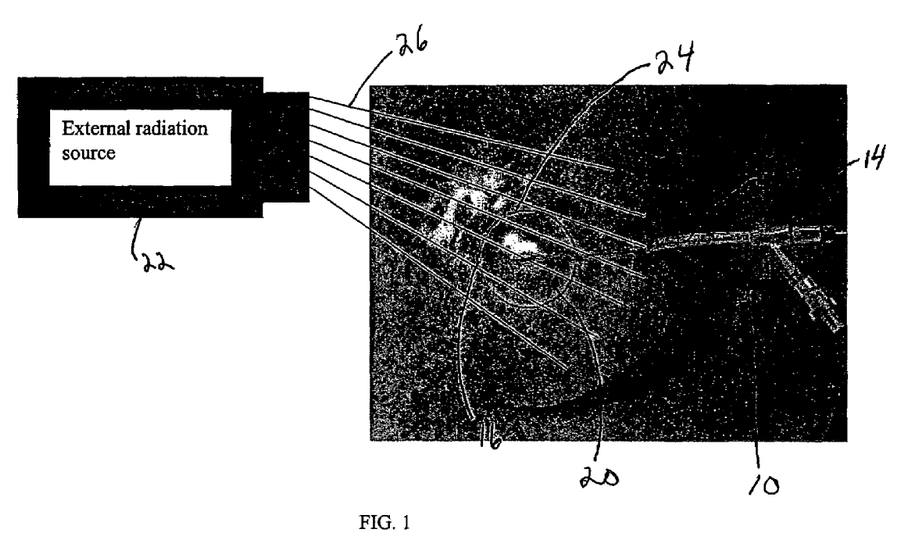
FIG. 1 illustrates the system of the present invention including an external radiation source and a tissue positioning device.

FIG. 1 illustrates one embodiment of the present invention including a system for treating tissue surrounding a resected cavity that is subject to a proliferative tissue disorder. The system includes a tissue fixation device 10 which includes a catheter body member 12 having a proximal end 14, a distal end 16, an inner lumen 18 (not shown), and an expandable surface element 20. Expandable surface element 20 is preferably disposed proximate to distal end 16 of catheter body member 12 and is sized and configured to reproducibly position tissue surrounding a resected tissue cavity in a predetermined geometry upon expansion. The system also includes an external radiation device 22 positioned outside the resected cavity such that external radiation device 22 can deliver a dose of radiation to the tissue surrounding expandable surface element 20. External radiation device 22 can be any external radiation source known in the art or later developed, however, in preferred embodiments of the invention, precisely targeted sources such as those used in 3DCRT and IMRT are employed. As shown in FIG. 1 tissue fixation device 10 can be positioned within a resected tissue cavity 24, in this example within a patient's breast following a lumpectomy, and expanded to position the surrounding tissue such that the dose of radiation beams 26 from external radiation device 22 is accurately delivered.

Figure 2:
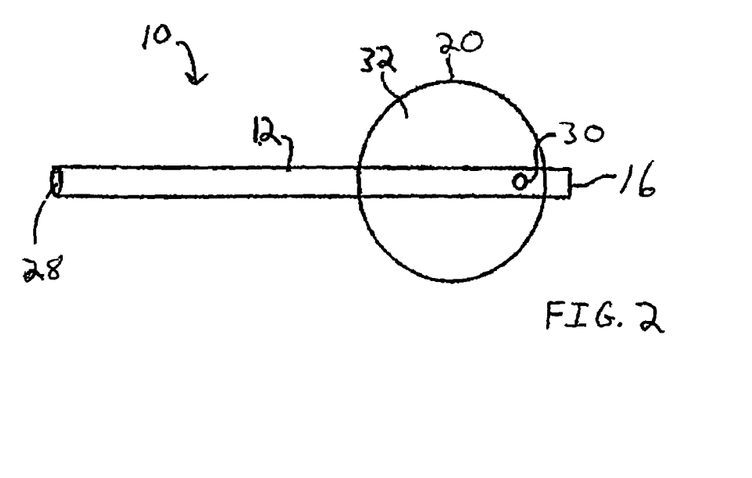
FIG. 2 illustrates one embodiment of the tissue positioning device which can be used with the system illustrated in FIG. 1.

FIGS. 2 through 8 illustrate exemplary embodiments of tissue positioning devices 10 which can work with the system of the present invention. FIG. 2 shows a basic design of a tissue positioning device 10, including an elongate body member 12 having an inner lumen 18 extending from proximal port 28 to inflation port 30. Inflation port 30 is formed through the side wall of body member 12 and intersects with inner lumen 18. Affixed to tubular body 12, proximate to a distal end 16 thereof, is a spatial volume 32 which is defined by an expandable surface 20. The interior of volume 32 is in fluid communication with proximal port 28.

Expandable surface 20 of device 10 can be defined by an inflatable balloon. It will be understood that the term "balloon" is intended to include distensible devices which can be, but need not be, constructed of an elastic material. The balloon of the present invention may include the variety of balloons or other distensible devices designed for use with surgical catheters. The balloon can be expanded by injecting an inflation material through body 12 and into the balloon, and preferably, the inflation material comprises non-radioactive liquids or gases. Alternatively, the inflation material is a treatment material, such as a radioactive treatment material where the balloon will also be used to provide interstitial brachytherapy treatment as is provided in U.S. Pat. Nos. 5,611,923 and 5,931,774 to Williams et al, both of which are incorporated by reference herein.

In one embodiment, the balloon is constructed of a solid material that is substantially impermeable to active components of a treatment fluid with which it can be filled, and is also impermeable to body fluids, e.g., blood, cerebrospinal fluid, and the like. An impermeable balloon is useful in conjunction with a radioactive treatment fluid, to prevent the radioactive material from escaping the treatment device and contaminating the surgical field or tissues of the patient.

In another embodiment, the balloon is permeable to a treatment fluid, and permits a treatment fluid to pass out of device 10 and into a body lumen or cavity. A permeable balloon is useful when the treatment fluid is a drug such as for example, a chemotherapeutic agent which must contact tissue to be effective. U.S. Pat. Nos. 5,611,923 and 5,931,774 to Williams et al. disclose exemplary permeable balloons and treatment substances. Semi-permeable balloons can also find use in the method of the present invention. For example, a semipermeable material that is capable of preventing the passage of a radioactive material through the balloon wall can be used to contain a treatment fluid, where certain fluid components can pass through the membrane while the radioactive components of the treatment fluid are retained within the balloon.

Although the balloon and body member 12 can mate in a variety of ways, in some embodiments, the balloon is mated to body member 12 at substantially a single point on, or a single side of, the balloon body. Such attachment permits the balloon (e.g., a spherical balloon) to maintain a substantially constant (e.g., spherical) shape over a range of inflation volumes. That is, the balloon is not constrained in shape by multiple attachment points to the body member, as is commonly the case with, e.g., balloons for Foley catheters. In other embodiments, the balloon is attached to the body member at multiple points on the balloon body, while allowing the balloon to maintain a constant shape over a range of inflation sizes. For example, a balloon attached to a body member at both distal and proximal points on the balloon body can be unconstrained upon inflation where the body member includes an expansion element (e.g., a slidable engagement element) that permits the body member to adjust in length as the balloon expands or contracts. A balloon which maintains a substantially constant shape over a range of inflation volumes permits a surgeon to select a balloon with less concern over the size of the cavity.

Body member 12 of device 10 provides a means for positioning expandable surface 20 within the resected tissue cavity and provides a path for delivering inflation material (if used). Although the exemplary body members illustrated in the FIGS. have a tubular construction, one of skill in the art will appreciate that body member 12 can have a variety of shapes and sizes. Body members suitable for use in the invention can include catheters which are known in the art. Although body member 12 can be constructed of a variety of materials, in one embodiment the body member material is silicone, preferably a silicone that is at least partially radio-opaque, thus facilitating x-ray location of body member 12 after insertion of device 10. Body member 12 can also include conventional adapters for attachment to a treatment fluid receptacle and the balloon, as well as devices, e.g., right-angle devices, for conforming body member 12 to contours of the patient's body.

The position of the device 10 with in a patient's body can also be determined using fiducial markers 60. By positioning the markers on the device (for example on expandable surface member 20 or on body member 12), a user can determine the spatial position of the device and the surrounding target tissue. The spatial data can be used to correct errors in target tissue location by adjusting the patient's body location on the treatment couch or by altering the radiotherapy beams' shape and direction. Fiducial markers are discussed in more detail below.

Device 10 can also include a variety of alternative embodiments designed to facilitate tissue positioning. For example, device 10 can include multiple spatial volumes, as well as, a variety of shapes adapted to conform and shape the resected cavity. In addition, the expandable surface can be positioned on and mated with tubular body member 12 in various ways to facilitate placement of the expandable surface within a tissue cavity. The expandable surface can also be adapted to allow delivery of a treatment material to the tissue surrounding the cavity.

Figure 3:
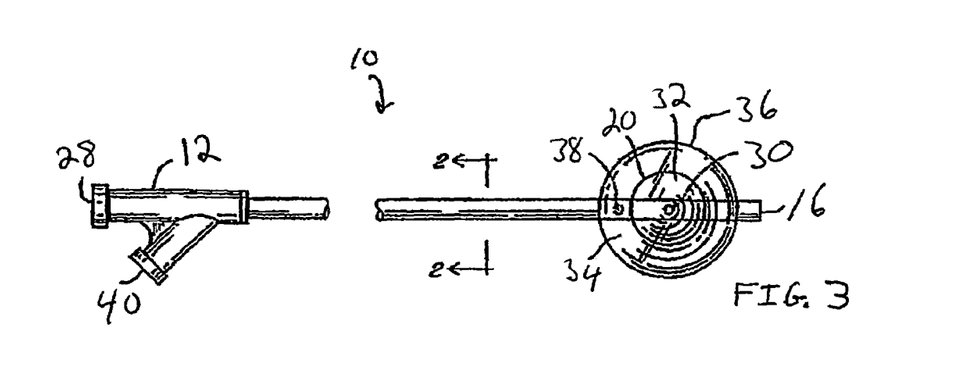
FIG. 3 illustrates another embodiment of the tissue positioning device which can be used with the system illustrated in FIG. 1.
Figure 3A:
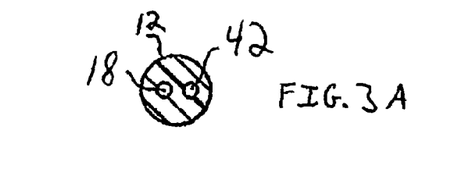
FIG. 3A illustrates a cross sectional view of the device pictured in FIG. 3.
Figure 4:
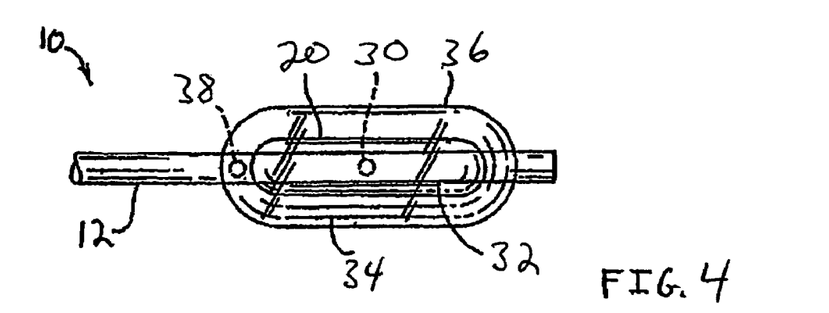
FIG. 4 illustrates another embodiment of the tissue positioning device which can be used with the system illustrated in FIG. 1.

The invention also contemplates the use of multiple balloons, e.g., a double-walled structure as shown in FIGS. 3 and 4. Such a balloon can comprise, for example, an impermeable inner wall and a permeable outer wall. In this embodiment, the inner balloon can be filled with, e.g., a radioactive treatment fluid, while the outer balloon (i.e., the space between the inner and outer balloon walls) is filled with a chemotherapeutic treatment fluid. This embodiment allows multiple modes of therapy (e.g., chemotherapy, brachytherapy and external radiation) to be administered with a single device. In this double-walled balloon embodiment the two balloons can be inflated with two treatment fluids at the same time or at different times during therapy. Inflation of an inner balloon can provide pressure on an outer balloon, which can cause the outer balloon to expand, or can force or urge fluid in the space between the inner and outer balloon walls through the membrane of a porous outer balloon. Higher-order balloons, e.g., triple-walled balloons, can also be used in the inventive devices. FIG. 3 illustrates an embodiment of device 10 with a second spatial volume 34 surrounding the inner spatial volume 32 and is defined by a second expandable surface 36. The second spatial volume is in fluid communication with a second inflation port 38 and a second proximal port 40. Body 12 also includes a second inner lumen 42 extending from proximal port 40 to inflation port 38. FIG. 3A illustrate inner lumen 18 and second inner lumen 42.

As shown by FIG. 4, the expandable surface can include a variety of shapes. For example, a generally spherical cavity can be filled and made to conform to a substantially spherical expandable surface, while it may be preferable to use an elongated expandable surface to position tissue surrounding an elongated body cavity. FIG. 4 illustrates an exemplary elongate expandable surface. In some cases, it may be desirable to use an expandable surface which has a different shape than that of the resected cavity so that when expanded, the expandable surface applies increased relative pressure to part of the cavity wall, e.g. applies pressure to a problem area. One of skill in the art will appreciate that the inner and outer expandable surfaces 20, 36 may define a variety of shapes depending on the form of the original resected cavity and on the desired shape of the cavity after conforming to the expandable surface, including by way of non-limiting example, a cube, a parallelepiped, a cylinder, a tetrahedron, a prism, an irregular shape or combinations thereof.

Figure 5A:
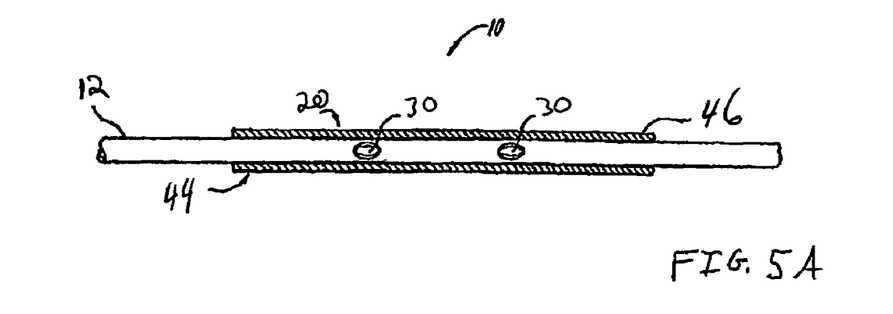
FIG. 5A illustrates another embodiment of the tissue positioning device which can be used with the system illustrated in FIG. 1.
Figure 5B:
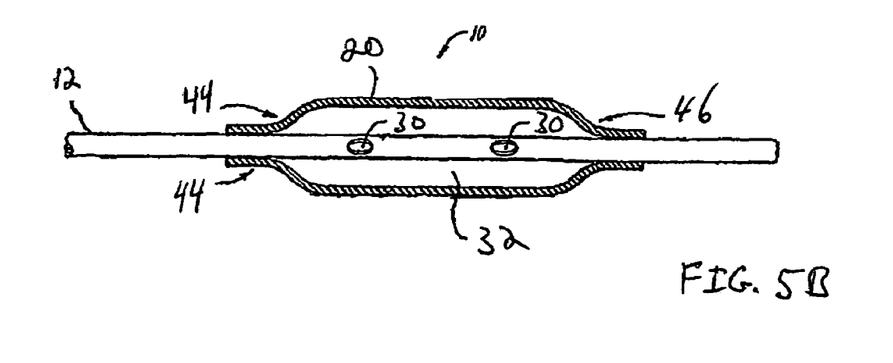
FIG. 5B illustrates the device of FIG. 5A in an expanded position.

In FIGS. 5A and 5B, yet another embodiment of device 10 is depicted in its unexpanded and expanded form. Device 10 includes an elongated flexible tubular body 12 having at least one inner lumen 18 extending the length thereof from a proximal end to a distal end. Openings in the side wall of body member 12 define one or more inflation ports 30 that provide fluid communication between inner lumen 14 and a spatial volume 32. Expandable surface 20 can be attached to the tubular body member 12 by bonding the proximal and distal ends 44, 46 of the expandable surface 22 to the tubular body 12. As shown in FIG. 4B, injecting an inflation material into the proximal end of catheter body 12 forces the inflation material to flow through inner lumen 18, out the inflation ports 30, and to fill spatial volume 32 within expandable surface 20, thereby inflating expandable surface 20.

Figure 6A:
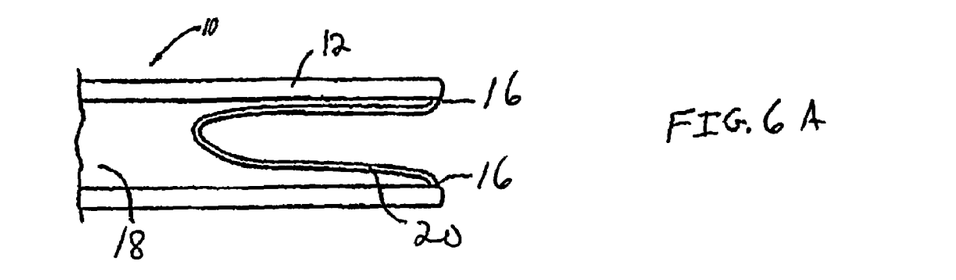
FIG. 6A illustrates another embodiment of the tissue positioning device which can be used with the system illustrated in FIG. 1.
Figure 6B:
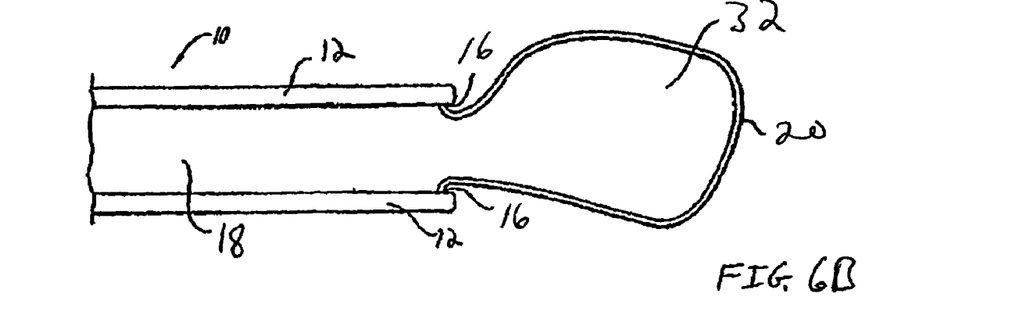
FIG. 6B illustrates the device of FIG. 6A in an expanded position.

In FIG. 6A, yet a further embodiment of device 10 is depicted, having an expandable surface 20 which resides within inner lumen 18 of tubular body 12. In this embodiment, the inner lumen 18 extends the length of body 12 and expandable surface 20 is fixedly attached at distal end 16 body 12. As an inflation material is injected through inner lumen 18, expandable surface 20 expands outwardly from tubular body 12 as shown in FIG. 6B. This device may be particularly advantageous for positioning tissue surrounding a spherical tissue cavity because the expandable surface can hold a generally spherical shape over a range of volumes. In addition, the embodiment of FIGS. 6A, 6B may be desirable when body member 12 of device 10 is positioned proximate to a body cavity prior to expanding.

Figure 7:
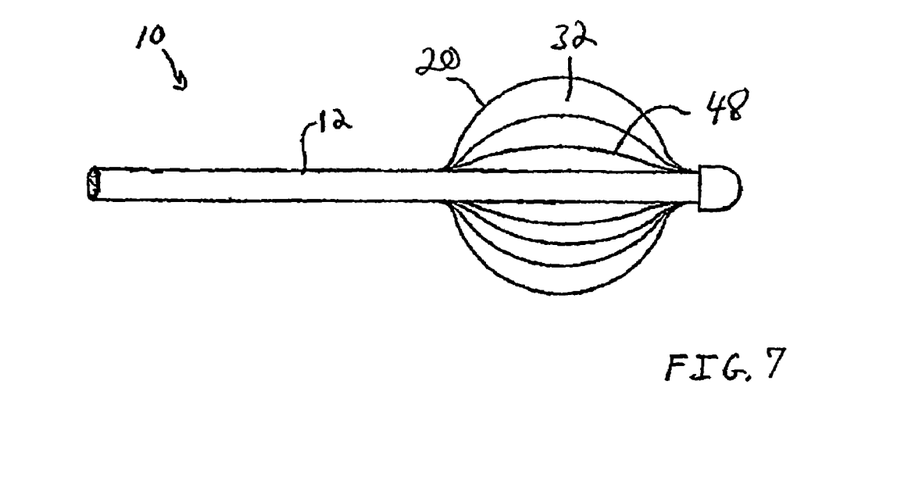
FIG. 7 illustrates another embodiment of the tissue positioning device which can be used with the system illustrated in FIG. 1.

Expandable surface 20 can be defined by a variety of structures, including a cage 48, as illustrated in FIG. 7. Similar to other embodiments, device 10 includes a body member 12 and an expandable surface 20, but expandable surface 20 is defined by cage 48, positioned proximal to the distal end of body member 12. Preferably, cage 48 is formed from a shape memory metal, such a nitinol, or a suitable plastic, such as an expandable polyethylene cage. In use the cage can be formed in the desired shape to conform to a particular resected cavity, contracted for delivery to the target site in vivo, and then expanded to cause the tissue surrounding the surgically resected region to take the appropriate shape.

Figure 8:
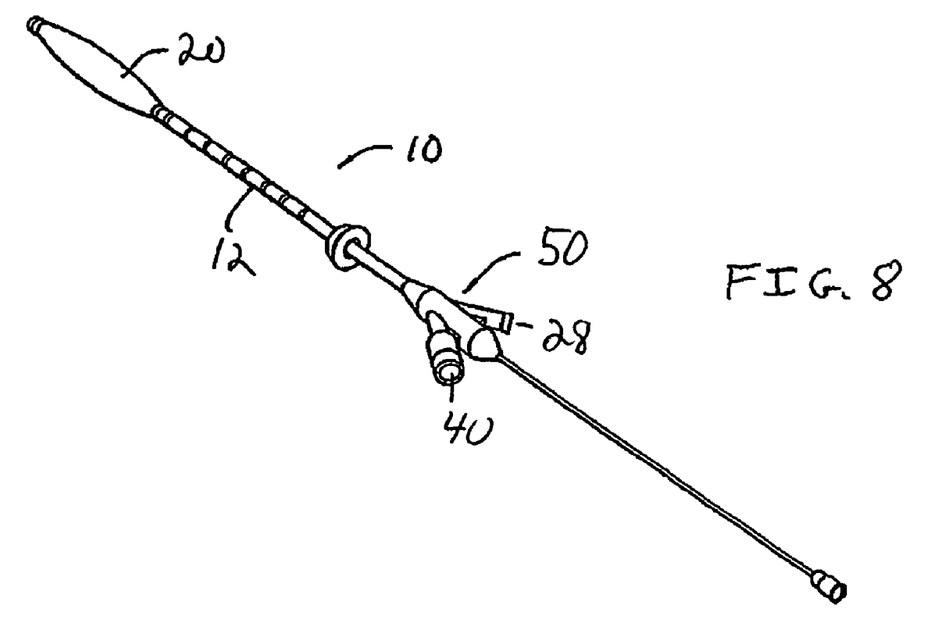
FIG. 8 illustrates another embodiment of the tissue positioning device which can be used with the system illustrated in FIG. 1.

FIG. 8 depicts a perspective view of one preferred embodiment of device 10 including body member 12 and expandable surface 20. The device includes inner (not shown) and outer expandable surfaces 20, 36, which are attached to body member 12, proximal to the distal end. Body member 12 includes first and second inner lumens and a control handle 50 at the proximal end for positioning of the device within a body cavity. Proximal ports 28, 40 provide entrances for inflation materials and/or treatment materials.

In some embodiments, the inventive devices are provided in pre-assembled form, i.e., the components are assembled in advance of a surgical insertion procedure. In certain embodiments, however, the inventive devices are configured to permit modular assembly of components, e.g., by a surgeon. Thus, for example, a treatment fluid receptacle can be provided with an element adapted for connection to any one of a plurality of catheters. The connection element can be, e.g., any element known in the art for effecting connection between components such as catheters, injection ports, and the like. Illustrative connectors include luer adapters and the like. In this embodiment, a variety of catheters and balloons can be provided, each of which is adapted for facile connection to the treatment fluid receptacle. The surgeon can then select an appropriate size and shape of expandable surface (e.g. balloon) for treatment of a particular proliferative disorder without need for providing several treatment fluid receptacles. The catheter and balloon can be selected according to the results of pre-operative tests (e.g., x-ray, MRI, and the like), or the selection can be made based on observation, during a surgical procedure, of the target cavity (e.g., a surgical cavity resulting from tumor excision). When the surgeon selects an appropriate balloon (e.g., a balloon having a size and shape suitable for placement in a body cavity), the catheter and balloon can then be attached to the pre-selected treatment fluid receptacle, thereby assembling the treatment device.

A method of the present invention can be used to treat a variety of proliferative tissue disorders including malignant breast and brain tumors. Many breast cancer patients are candidates for breast conservation surgery, also known as lumpectomy, a procedure that is generally performed on early stage, smaller tumors. Breast conservation surgery may be followed by radiation therapy to reduce the chance of recurrences near the original tumor site. Providing a strong direct dose to the effected area can destroy remaining cancer cells and help prevent such recurrences.

Surgery and radiation therapy are also the standard treatments for malignancies which develop in other areas of the body such as brain tumors. The goal of surgery is to remove as much of the tumor as possible without damaging vital brain tissue. The ability to remove the entire malignant tumor is limited by its tendency to infiltrate adjacent normal tissue. Partial removal reduces the amount of tumor to be treated by radiation therapy and, under some circumstances, helps to relieve symptoms by reducing pressure on the brain.

A method according to the invention for treating these and other malignancies begins by surgical resection of a tumor site to remove at least a portion of the cancerous tumor and create a resection cavity. Following tumor resection, device 10 is placed into the tumor resection cavity. This can occur prior to closing the surgical site such that the surgeon intraoperatively places the device, or alternatively device 10 can be inserted once the patient has sufficiently recovered from the surgery. In the later case, a new incision for introduction of device 10 can be created. In either case, expandable surface 20, which is preferably sized and configured to reproducibly position tissue surrounding the resection cavity in a predetermined geometry, is then expanded within the resected tissue cavity. Where expandable surface 20 is defined by a balloon, the balloon can be expanded by delivering an inflation material through the inner lumen 18 into the balloon to expand the balloon.

Expandable surface 20 can be selected such that, upon expansion, expandable surface 20 compresses the tissue which is being treated, or the surrounding tissues. Thus, where expandable surface 20 is a balloon, it can be selected to have a desired size, and the amount of injected material can be adjusted to inflate the balloon to the desired size. When inflated expandable surface 20 preferable fills a volume of at least about 4 cm$^3$, and even more preferably it is capable of filling a volume of at least about 35 cm$^3$. Preferable inflation volumes range from 35 cm$^3$ to 150 cm$^3$. In general, when deflated the balloon should have a small profile, e.g., a small size to permit facile placement in and removal from the patient's body and to minimize the size of a surgical incision needed to place and remove the balloon at the desired site of action.

With device 10 expanded, it supports the tissue surrounding the tissue cavity and reduce tissue shifting. In addition, expandable surface 20 can position the tissue in a predetermined geometry. For example, a spherical expandable surface can position the tissue surrounding the tissue cavity in a generally spherical shape. With the tissue positioned, a defined surface is provides so that radiation can more accurately be delivered to the previously irregular tissue cavity walls. In addition, device 10 helps reduce error in the treatment procedure introduced by tissue movement. The positioning and stabilization provided by device 10 greatly improves the effectiveness of radiation therapy by facilitating radiation dosing and improving its accuracy. The result is a treatment method which concentrates radiation on target tissue and helps to preserve the surrounding healthy tissue.

Prior to delivering radiation, but after expanding the expandable surface, device 10 and the surrounding tissue can preferably be visualized with an imaging device, including by way of non-limiting example, x-ray, MRI, CT scan, PET, SPECT and combinations thereof. These imaging devices provide a picture of the device 10 and the surrounding tissue to assist with the planning of external radiation therapy. To aid with visualization, device 10 can be constructed of materials which highlight expandable surface 20 during the imaging procedure, for example, the expandable surface may be constructed of a radio opaque material. Alternatively, radiation transparent materials can used so that tissue imaging is not blocked by the expandable surface. In either embodiment, the expandable surface can be inflated with a diagnostic imaging agent, including radioactive ray absorbent material, such as air, water or a contrast material.

In the case of external radiation therapies such as 3DCRT and IMRT, the imaging procedures provide a map of the residual tissue margin and assist with targeting tissue for radiation dosing. The radiation beams are then adapted for delivering a very precise radiation dose to the target tissue. With device 10 positioning the tissue surrounding the resection cavity, there is less danger of the target tissue shifting (within the body) and thus having the planned radiation missing the PTV and needlessly damaging healthy tissue.

Some treatment regimens require repeated radiation dosing over a course of days or weeks, and device 10 can be used in those cases to repeatedly position the tissue surrounding the resected tissue cavity. For example, after delivering radiation from the external source, the expandable surface is collapsed. Although device 10 can be removed after the step of collapsing, preferably the device is left within the tissue cavity between radiation treatments. When a subsequent radiation treatment is to be delivered, the expandable surface can be expanded and the adjacent tissue can be repositioned for another imaging step and/or radiation dose. These steps can be repeated as necessary over a course of a treatment regimen. Alternatively, the device is left within the tissue cavity and is maintained at a generally constant volume of expansion/inflation during an entire course of radiation therapy.

Another embodiment of the invention incorporates fiducial markers that provide real-time, wireless information about the device's spatial position relative to the origin of a coordinate system in the treatment room (e.g., the isocenter of the radiation delivery device or the radiation beam's source location). The spatial position data can be used to correct errors in target volume location. For example, by adjusting the patient's body position on the treatment couch and/or altering the radiotherapy beams' shape and direction to correct for the altered PTV position. Preferably, the real-time, wireless feedback allows correction of positioning errors prior to delivery of each fraction of radiation. Fiduciary markers can also provide users more a more accurate PTV position and thereby allow greater normal tissue sparing and smaller normal tissue margins within the PTV. Preferably, the fiducial markers and their detection systems are radio-opaque markers that are imaged radiographically (e.g., fluoroscopically) or transponders that signal their positions to a receiver system. An exemplary fiducial marker is the Beacon Transponder, made by Calypso Medical Technologies of Seattle, Wash.

Positioning fiducial markers 60 on device 10 provides an advantage over other placements of such markers (e.g. placement within a tumor). For example, by placing a fiducial marker on expandable surface member 20, the position of the expandable surface can be precisely determined and the amount of expansion can be adjusted. In addition, a marker positioned on the outside of device 10 can be used to delineate the surrounding target tissue (a.k.a. the PTV). As an additional benefit of having the marker positioned on the device, a separate insertion step is not required for the marker. Also, when the device is removed, the marker will also be removed, thereby assuring that foreign objects are not left permanently in the patient at the conclusion of the treatment.

In addition to external radiation, other treatments can supplement the method of the present invention. In one embodiment, a brachytherapy treatment is combined with the external radiation therapy of the present invention by delivering a radiation source through body member 12 into expandable surface 20 so that the resection cavity is irradiated from the inside. Brachytherapy procedures are disclosed in U.S. Pat. No. 6,413,204 to Winkler et al. commonly assigned and incorporated herein by reference. Other treatments can include supplying treatment material to the tissue surrounding the resection cavity, e.g. a chemotherapy drug, or a radiation enhancing material. In one embodiment, the treatment material can be delivered through the wall of the expandable surface which is constructed of permeable hydrophilic polymer as disclosed in U.S. Pat. No. 6,200,257 to Winkler, commonly assigned and incorporated herein by reference.

Alternatively, the treatment material may be mated to the expandable surface such that after insertion of device 10, expandable surface 20 delivers the treatment material to surrounding tissue. The treatment material can diffuise from expandable surface 20 to tissue and/or the treatment material may be delivered as the expandable surface presses against the resected cavity walls and contacts tissue. In yet a further embodiment, the treatment material may be positioned on only part of the expandable surface. Regardless of the method of delivery, the treatment materials may include, by way of non-limiting example, a chemotherapy agent, an anti-neoplastic agent, an anti-angiogenesis agent, an immunomodulator, a hormonal agent, an immunotherapeutic agent, an antibiotic, a radiosensitizing agent, and combinations thereof.

A person of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entity.

What is claimed is:

1. A method for treating a proliferative tissue disorder, comprising:
   (a) surgically resecting at least a portion of the proliferative tissue and thereby creating a resection cavity;
   (b) providing a tissue fixation device having an expandable surface sized and configured to reproducibly position tissue surrounding the resection cavity in a predetermined geometry which is substantially constant over a range of inflation volumes upon expansion of the expandable surface into an expanded position;
   (c) positioning the tissue fixation device so that the expandable surface is within the resection cavity;
   (d) expanding the expandable surface to position the tissue surrounding the resection cavity in the predetermined geometry; and
   (e) applying an external radiation treatment to the tissue surrounding the resection cavity.

2. The method of claim 1, wherein the expandable surface of the tissue fixation device includes a solid distensible surface defining a closed distensible chamber.

3. The method of claim 2, wherein the tissue fixation device is a balloon catheter.

4. The method of claim 3, wherein a second balloon is positioned within the first balloon.

5. The method of claim 2, wherein the medium used to expand the balloon consists of a non-radioactive substance.

6. The method of claim 2, wherein a treatment material is disposed on the outer surface of the solid distensible surface.

7. The method of claim 6, wherein a treatment material is disposed on only part of the outer surface of the solid distensible surface.

8. The method of claim 2, wherein the solid distensible surface is radiation transparent.

9. The method of claim 1, wherein a fiducial marker is positioned on the tissue fixation device.

10. The method of claim 9, wherein the fiducial marker is radio-opaque and imaging is provided radiographically.

11. The method of claim 9, wherein the fiducial marker is a signal transponder whose signals are read and interpreted by a receiver.

12. The method of claim 2, wherein a fiducial marker is positioned on the solid distensible surface.

13. The method of claim 1, wherein the expandable surface is defined by an expandable hydrophilic polymer membrane having a predetermined permeability.

14. The method of claim 13, wherein a treatment material diffuses through the expandable hydrophilic polymer membrane after the step of positioning the tissue fixation device.

15. The method of claim 1, wherein the expandable surface is created by an expandable cage.

16. The method of claim 15, wherein the expandable cage comprises a shape memory material.

17. The method of claim 1, wherein the step of expanding expands the expandable surface so that it substantially fills the volume of the resected cavity and presses against the walls of the resected cavity.

18. The method of claim 1, wherein the step of surgically resecting is performed during a lumpectomy procedure.

19. The method of claim 1, wherein before the step of applying the external radiation treatment, the resected cavity and the tissue fixation device positioned within the resected cavity are visualized in three dimensions.

20. The method of claim 1, wherein the external radiation treatment is an external beam radiation treatment.

21. The method of claim 1, wherein the external radiation treatment is a three-dimensional conformational radiation therapy treatment.

22. The method of claim 1, wherein the external radiation treatment is an intensity modulation radiation therapy treatment.

23. The method of claim 1 wherein the expandable surface is maintained in an inflated state throughout the duration of radiation therapy.

24. The method of claim 1, wherein after applying a first radiation fraction of the external radiation treatment the expandable surface is collapsed.

25. The method of claim 24, wherein the expandable surface is expanded a second time to position tissue surrounding the resection cavity.

26. The method of claim 25, wherein a second fraction of the external radiation treatment is applied after the expandable surface is expanded a second time.

27. The method of claim 1, further comprising,
   removing the tissue fixation device from the surgically resection cavity;
   inserting a tissue fixation device having an expandable surface within the resection cavity; and
   expanding the expandable surface to position the tissue surrounding the resection cavity in a predetermined geometry.

28. A system for treating tissue surrounding a resected cavity that is subject to a proliferative tissue disorder, comprising:
   a tissue fixation device including a catheter body member having a proximal end, a distal end, an inner lumen, and an expandable surface element disposed proximate to the distal end of the body member, the expandable surface element sized and configured to reproducibly position tissue surrounding a resected tissue cavity in a predetermined geometry which is substantially constant over a range of inflation volumes upon expansion; and an external radiation device positioned outside the resected cavity such that the external radiation device can deliver a dose of radiation to the tissue surrounding the expandable surface element, wherein the tissue fixation device can be positioned within a resected tissue cavity and expanded to position the surrounding tissue such that the delivery of a radiation beam from the external radiation device is accurately delivered.

29. The system of claim 28, wherein the expandable surface element is a solid distensible surface and the spatial volume is a closed, distensible chamber and the expandable surface element is a radiation transparent wall.

30. The system of claim 29, wherein the medium used to expand the expandable surface element consists of a non-radioactive gas.

31. The system of claim 28, wherein the expandable surface is created by an expandable cage.

32. The system of claim 31, wherein the expandable cage comprises a shape memory material.

33. The system of claim 28, wherein the resection cavity is created during a lumpectomy procedure.

34. The system of claim 28, wherein the external radiation source is an external beam radiation device.

35. The system of claim 28, wherein the external radiation source is a three-dimensional conformational radiation therapy device.

36. The system of claim 28, wherein the external radiation source is an intensity modulation radiation therapy device.

37. The system of claim 28, wherein a fiducial marker is positioned on the tissue fixation device.

38. A device for treating a proliferative tissue disorder after a lumpectomy procedure, comprising:

an elongate body member having an open proximal end defining a proximal port, a distal end and an inner lumen extending from the open proximal end, the elongate body member being sized for delivering an expandable surface element into a resection cavity created by a lumpectomy procedure;

a spatial volume defined by an expandable surface element disposed proximate to the distal end of the body member, the expandable surface element sized and configured to reproducibly position tissue surrounding a resected tissue cavity in a predetermined geometry which is substantially constant over a range of inflation volumes upon expansion;

wherein the expandable surface element is size to fill a tissue cavity created in a breast during a lumpectomy procedure so as to position the surrounding tissue and allow an external radiation source to accurately deliver a dose of radiation.

39. The device of claim 38, wherein a fiducial marker is positioned on the tissue fixation device.

40. The device of claim 39, wherein the fiducial marker is radio-opaque and imaging is provided radiographically.

41. The device of claim 39, wherein the fiducial marker is a signal transponder whose signals are read and interpreted by a receiver.

42. The device of claim 38, wherein a fiducial marker is positioned on the expandable surface element.

* * * * *